(12) United States Patent
Strobl (10) Patent No.: US 10,881,446 B2
(45) Date of Patent: Jan. 5, 2021

(54) VISUAL DISPLAYS OF ELECTRICAL PATHWAYS

(71) Applicant: Ethicon LLC, Guaynabo, PR (US)

(72) Inventor: Geoffrey S. Strobl, Williamsburg, OH (US)

(73) Assignee: Ethicon LLC, Guaynabo, PR (US)

( * ) Notice: Subject to any disclaimer, the term of this patent is extended or adjusted under 35 U.S.C. 154(b) by 199 days.

(21) Appl. No.: 15/383,147

(22) Filed: Dec. 19, 2016

(65) Prior Publication Data

US 2018/0168715 A1    Jun. 21, 2018

(51) Int. Cl.
| | |
|---|---|
| *A61B 18/12* | (2006.01) |
| *A61B 18/14* | (2006.01) |
| *A61B 18/16* | (2006.01) |
| *A61B 90/00* | (2016.01) |
| *A61B 34/35* | (2016.01) |
| *A61B 17/29* | (2006.01) |
| *A61B 17/295* | (2006.01) |
| *A61B 34/30* | (2016.01) |

(52) U.S. Cl.
CPC .......... *A61B 18/1206* (2013.01); *A61B 17/29* (2013.01); *A61B 18/1445* (2013.01); *A61B 18/16* (2013.01); *A61B 34/35* (2016.02); *A61B 90/08* (2016.02); *A61B 90/361* (2016.02); *A61B 90/37* (2016.02); *A61B 17/295* (2013.01); *A61B 18/1233* (2013.01); *A61B 2017/2926* (2013.01); *A61B 2018/1452* (2013.01); *A61B 2018/162* (2013.01); *A61B 2034/301* (2016.02); *A61B 2090/0811* (2016.02)

(58) Field of Classification Search
CPC ... A61B 17/29; A61B 17/295; A61B 18/1206; A61B 18/1233; A61B 18/1445; A61B 18/16; A61B 2017/2926; A61B 2018/1452; A61B 2018/162
See application file for complete search history.

(56) References Cited

U.S. PATENT DOCUMENTS 5,403,312 A * 4/1995 Yates ............... A61B 17/07207
606/50
5,443,463 A * 8/1995 Stern ...................... A61B 18/14
606/51

(Continued)

FOREIGN PATENT DOCUMENTS

WO   WO-9848687 A2   11/1998
WO   WO-2014151621 A1   9/2014

OTHER PUBLICATIONS

International Search Report and Written Opinion for International App. No. PCT/US2017/064420 dated May 11, 2018 (17 pages).

(Continued)

*Primary Examiner* — Daniel W Fowler
(74) *Attorney, Agent, or Firm* — Mintz Levin Cohn Ferris Glovsky and Popeo, P.C.

(57) ABSTRACT

Surgical tools are provided herein that have a housing and an elongate tool shaft extending from the housing with an end effector on a distal end thereof. The end effectors deliver electrical energy onto and/or through tissue, and the end effectors are configured to display at least one location of one or more paths of the electrical energy through the end effector.

18 Claims, 4 Drawing Sheets

(56) References Cited

U.S. PATENT DOCUMENTS

| | | | | |
|---|---|---|---|---|
| 5,693,051 | A | * | 12/1997 | Schulze ............ A61B 17/07207 606/51 |
| 8,114,345 | B2 | | 2/2012 | Dlugos, Jr. et al. |
| 8,568,411 | B2 | * | 10/2013 | Falkenstein ......... A61B 18/1445 606/51 |
| 2003/0109876 | A1 | * | 6/2003 | Yamauchi ........... A61B 18/1442 606/48 |
| 2005/0203507 | A1 | | 9/2005 | Truckai et al. |
| 2011/0028964 | A1 | * | 2/2011 | Edwards ............ A61B 18/1442 606/33 |
| 2012/0209288 | A1 | * | 8/2012 | Robinson ............... A61B 34/30 606/130 |
| 2014/0104070 | A1 | | 4/2014 | Plaven |
| 2014/0163549 | A1 | * | 6/2014 | Yates ................ A61B 18/1445 606/41 |
| 2015/0073406 | A1 | * | 3/2015 | Molsberger ............ A61N 1/205 606/41 |
| 2015/0282868 | A1 | * | 10/2015 | Keller ................ A61B 18/1445 606/52 |
| 2016/0166336 | A1 | | 6/2016 | Razzaque et al. |

OTHER PUBLICATIONS

International Preliminary Report on Patentability received for PCT International Application No. PCTUS2017064420, dated Jul. 4, 2019, 13 pages.

* cited by examiner

VISUAL DISPLAYS OF ELECTRICAL PATHWAYS

FIELD

Methods and devices are provided for displaying electrical pathways in end effectors of surgical tools.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient while viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery, such as for displaying electrical pathways in end effectors of surgical tools.

SUMMARY

Methods and devices are provided for displaying electrical pathways in end effectors of surgical tools. In one aspect, a surgical tool is provided that includes an elongate shaft and an end effector at a distal end thereof. The end effector has one or more electrodes. Each electrode is configured to have electrical energy pass therethrough, and the end effector is configured to display at least one location of one or more paths of the electrical energy through the end effector.

The tool can vary in numerous ways. For example, the end effector can have at least two electrodes. Each electrode can have different electrical potentials. The end effector can have visual indicators configured to display the location of the one or more paths of the electrical energy indicating one or more active energy paths and corresponding return paths. In another example, the visual indicators can include at least one of pad printed symbols, chemical etchings, dip painting, screen printing, laser engraving, indenting, injection molding, mechanical engraving, abrasive blasting, embossing, coining, broken lines, solid lines, and a grid work on at least one surface of the end effector. The end effector can also include at least one active electrode and at least one return electrode configured to pass the electrical energy therethrough. The end effector can include upper and lower jaws and at least one active electrode and at least one return electrode. The at least one active electrode and the at least one return electrode can be positioned together on at least one of the upper jaw and the lower jaw. In another example, the tool can include a system with a processor, a display, and a camera. The system can be configured to virtually display the at least one location of one or more paths of the electrical energy on a display screen. The end effector can include upper and lower jaws, a plurality of teeth on one of the upper and the lower jaw, and a corresponding groove configured to receive the teeth on the other of the upper and the lower jaw. The end effector can also include one or more lighting sources configured to illuminate at least one pathway of the electrical energy therethrough.

In another embodiment, a surgical tool is provided with a housing and an elongate shaft extending distally from the housing with an end effector coupled to a distal end thereof. The end effector is configured to grasp tissue and apply energy thereto. The surgical tool has at least one indicator on the end effector that is configured to indicate at least one location from which energy will be applied to tissue.

The surgical tool can have numerous variations. For example, the at least one indicator can include at least one visual marking on at least one surface of the end effector. The end effector can include at least two electrodes of different potentials and configured to apply energy to tissue. In another example, the end effector can include upper and lower jaws and can be configured to apply energy and receive return energy through only one of the upper jaw and the lower jaw. At least one indicator can include at least one of pad printed symbols, chemical etchings, dip painting, screen printing, laser engraving, indenting, injection molding, mechanical engraving, abrasive blasting, embossing, coining, broken lines, solid lines, and a grid work on at least one surface of the end effector. In another example, the end effector can include a cutting element configured to translate therethrough to cut tissue grasped by the end effector. The surgical tool can also include a robotic surgical system configured to releasably and replaceably couple to the surgical tool.

In another aspect, a surgical method is provided that includes applying energy to tissue through an end effector of a surgical tool. The end effector has one or more indicators to display a location of one or more electrical energy pathways therethrough that are used to apply the energy to the tissue.

The method can vary in numerous ways. For example, the end effector can include upper and lower jaws, and applying energy can include activating at least one first electrode that is positioned in only one of the upper jaw and the lower jaw. The same upper jaw or lower jaw can have at least one return electrode. In another example, the one or more indicators can include at least one of pad printed symbols, chemical etchings, dip painting, screen printing, laser engraving, indenting, injection molding, mechanical engraving, abrasive blasting, embossing, coining, broken lines, solid lines, and a grid work on at least one surface of the end effector. The method can include releasably and replaceably coupling the surgical tool to a robotic surgical system.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used. Additionally, WIPO Patent Publication No. WO2014/151621, filed on Mar. 13, 2014 and entitled "Hyperdexterous Surgical System," is incorporated herein by reference.

Various surgical tools are provided that include end effectors through which electrical energy (e.g., radio frequency energy) passes and on which electrical pathways are indicated. Robotic surgical tools generally have a housing and an elongate tool shaft extending from the housing with an end effector on a distal end thereof configured to grasp tissue. The housing has a plurality of actuators for causing various functions of the end effector, such as rotation, articulation, clamping, firing, stapling, etc. Many surgical tools have end effectors capable of delivering electrical energy into and/or through tissue for a variety of purposes, for example to seal tissue, for spot coagulation, for energy enhanced otomy creation, for surface ablation, etc. Because electrical paths through the end effectors remain constant, users can learn where the electrical paths are in the end effector through use and experience. However, this learning process can be time consuming, and the user may not be interested and/or able to devote time and effort to develop this expertise. End effectors are provided that are configured to deliver electrical energy to tissue and are configured to display at least one location of one or more paths of the electrical energy through the end effector. Alternatively or in addition, a surgical system can display a virtual representation of the end effector showing a location of one or more paths of electrical energy. By identifying a location of one or more paths of the electrical energy, the end effector can reduce or eliminate the time and effort required to learn where electrical paths are in various end effectors. Users can quickly and effectively use the surgical tools for operations such as spot coagulation, ablation, otomy creation, etc.

Figure 1:
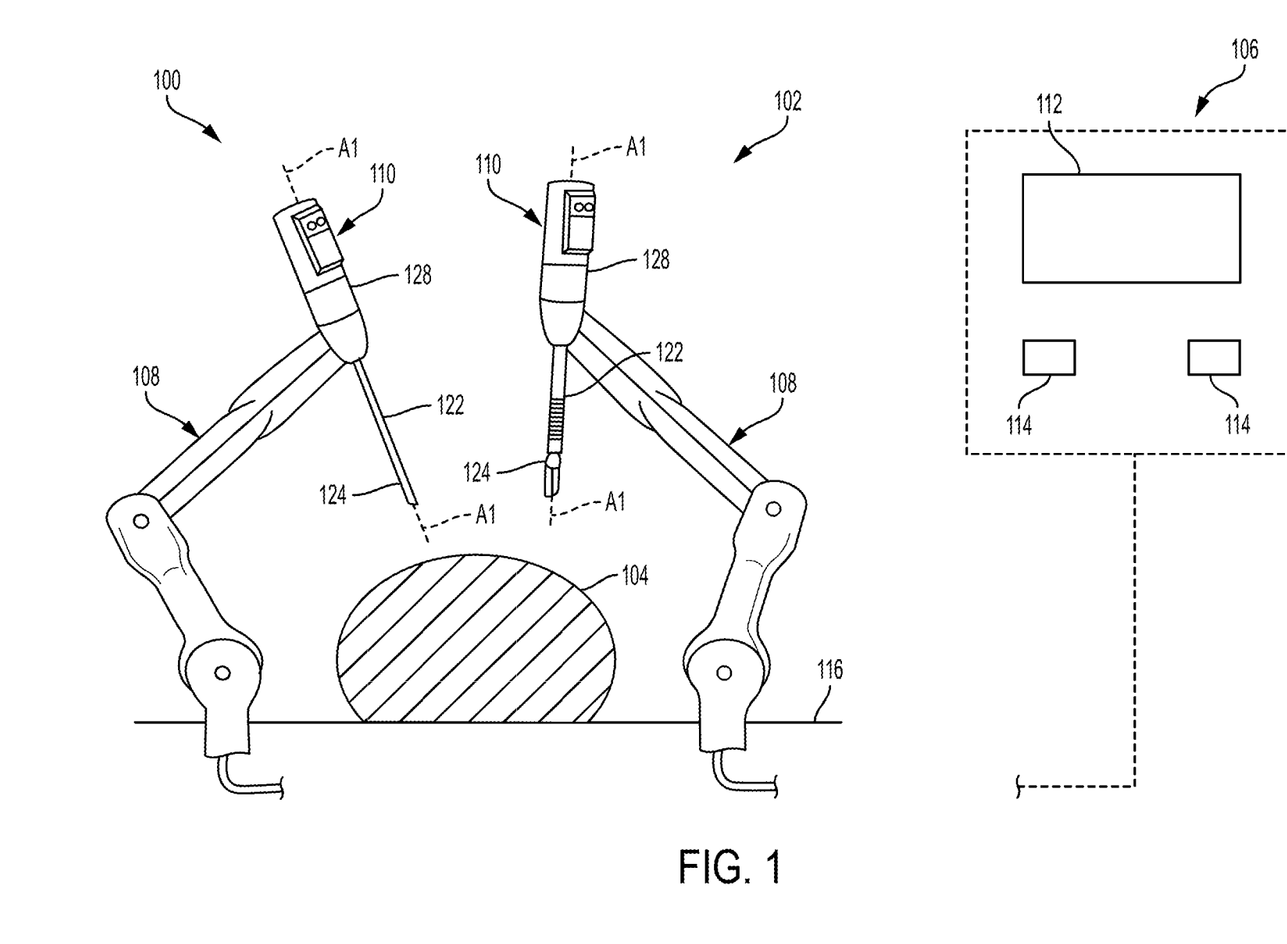
FIG. 1 is a perspective view of one embodiment of a surgical robotic system that includes a patient-side portion and a user-side portion.

FIG. 1 is a perspective view of one embodiment of a surgical robotic system 100 that includes a patient-side portion 102 that is positioned adjacent to a patient 104, and a user-side portion 106 that is located a distance from the patient, either in the same room and/or in a remote location. The patient-side portion 102 generally includes one or more robotic arms 108 and one or more surgical tools and/or tool assemblies 110 that are configured to releasably couple to a robotic arm 108. The user-side portion 106 generally includes a vision system 112 for viewing the patient 104 and/or surgical site, and a control system 114 for controlling the movement of the robotic arms 108 and each surgical tool 110 during a surgical procedure. The viewing system can display images of the surgical site captured by one or more cameras (not shown) present on the patient-side portion 102.

The surgical tool 110 includes an elongate shaft 122, an end effector 124, and a tool housing 128 coupled to a proximal end of the shaft 122. The end effector 124 is configured to move relative to the shaft 122, e.g., by pivoting, to position the end effector 124 at a desired location relative to a surgical site during use of the tool 110. The housing 128 includes various components (e.g., gears and/or actuators) configured to control the operation various features associated with the end effector 124 (e.g., any one or more of clamping, firing, rotation, articulation, energy delivery, etc.). The shaft 122, and hence the end effector 124 coupled thereto, is configured to rotate about a longitudinal axis A1 of the shaft 122. The various components of the housing 128 are configured to control the rotational movement of the shaft 122. In at least some embodiments, as in this illustrated embodiment, the surgical tool 110 is configured to releasably couple to the robotic arm 108, and the tool housing 128 can include coupling features configured to allow the releasable coupling of the tool 110 to the robotic arm 108. The surgical tool 110 can have any of a variety of configurations. In general, the surgical tool can be configured to perform at least one surgical function and can include any of, for example, forceps, a grasper, a needle driver, scissors, an electrocautery tool that applies energy, a stapler, a clip applier, a suction tool, an irrigation tool, an imaging device (e.g., an endoscope or ultrasonic probe), etc. The surgical tool 110 in at least some embodiments is configured to apply energy (such as radiofrequency (RF) energy) to tissue, while in other embodiments the tool 110 is not configured to apply energy to tissue.

The shaft 122 can have any of a variety of configurations. In general, the shaft 122 is an elongate member extending distally from the housing 128 and having at least one inner lumen extending therethrough. The shaft 122 is fixed to the housing 128, but in other embodiment the shaft 122 can be releasably coupled to the housing 128 such that the shaft 122 can be interchangeable with other shafts. This may allow a single housing 128 to be adaptable to various shafts having different end effectors.

The control system 114 can have a variety of configurations and can be located adjacent to the patient (e.g., in the operating room), remote from the patient (e.g., in a separate control room), or distributed at two or more locations (e.g., the operating room and/or separate control room(s)). As an example of a distributed system, a dedicated system control console can be located in the operating room, and a separate console can be located in a remote location. The control system 114 can include components that enable a user to view a surgical site of the patient 104 being operated on by the patient-side portion 102 and/or to control one or more parts of the patient-side portion 102 (e.g., to perform a surgical procedure at the surgical site). In some embodiments, the control system 114 can also include one or more manually-operated input devices, such as a joystick, exoskeletal glove, a powered and gravity-compensated manipulator, or the like. The one or more input devices can control teleoperated motors which, in turn, control the movement of the surgical system, including the robotic arms 108 and surgical tools 110.

The patient-side portion 102 can have a variety of configurations. As illustrated in FIG. 1, the patient-side portion 102 can couple to an operating table 116. However, in other embodiments, the patient-side portion 102 can be mounted to a wall, to the ceiling, to the floor, or to other operating room equipment. Further, while the patient-side portion 102 is shown as including two robotic arms 108, more or fewer robotic arms 108 may be included. Furthermore, the patient-side portion 102 can include separate robotic arms 108 mounted in various positions, such as relative to the operating table 116 (as shown in FIG. 1). Alternatively, the patient-side portion 102 can include a single assembly that includes one or more robotic arms 108 extending therefrom.

Figure 2:
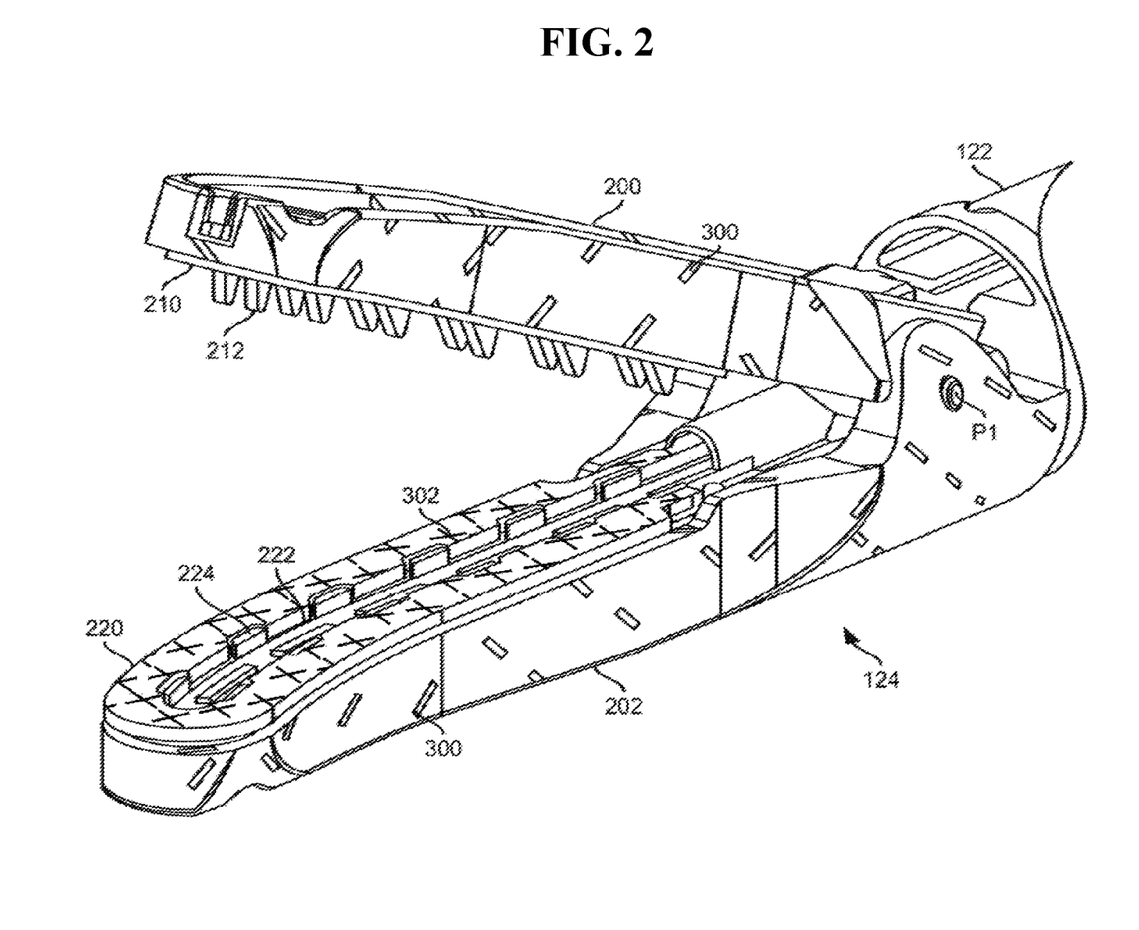
FIG. 2 is a perspective view of one embodiment of an end effector on a distal end of the surgical tool of FIG. 1.

While the surgical tool 110 can have a variety of end effectors, the end effector 124 illustrated in FIG. 2 can have first and second jaws 200, 202 configured to grasp tissue therebetween. At least one of the jaws 200, 202 can pivot between open and closed jaw configurations. As shown in FIG. 2, the first jaw 200 is configured to pivot with respect to the second jaw 202 and the shaft 122 about pivot point P1. The first jaw 200 has a first tissue contact surface 210 and one or more teeth 212 that extend along a length of the first jaw 200 on the first tissue-contacting surface 210. The second jaw 202 has a second tissue-contacting surface 220 and a groove 222 extending along a length of the second tissue-contacting surface 220. A plurality of protrusions 224 are formed inside the groove 222 and extend along either edge of the groove 222. The groove 222 is configured to receive the teeth 212 therein, and the teeth 212 and the plurality of protrusions 224 are configured to contact one another along corresponding side surfaces. The first jaw 200 is configured to move from an open configuration (shown in FIG. 2) to a closed configuration (not shown) in which it is moved closer to the second jaw 202 to enable to tissue to be grasped between the first jaw 200 and the second jaw 202.

Figure 2A:
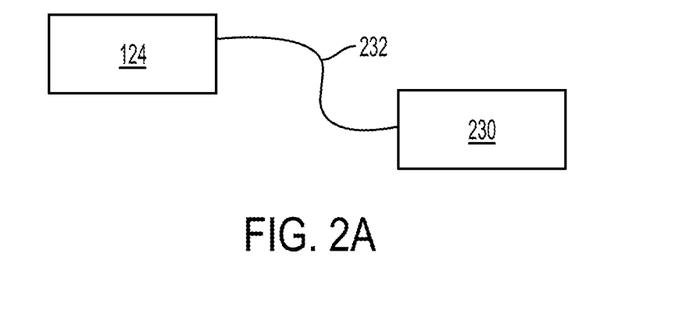
FIG. 2A is a diagram representative of the end effector of FIG. 2 connected to a power source.

As generally indicated by FIG. 2A, one or more electrical connectors 232 extend from an energy source 230 through the housing and to the end effector 124 to deliver energy (e.g., RF energy) to tissue and to serve as a return path. The energy source 230 can be an RF generator suitable for medical applications of a type well-known in the art.

As explained above, the end effector 124 has one or more electrical pathways therethrough so that, when tissue is grasped between the first and second jaws 200, 202, the end effector can be actuated to apply energy thereto. The end effector 124 is connected to an energy source 230 by one or more electrical connectors 232, as illustrated in FIG. 2A. In one embodiment, the end effector 124 has at least one active or positive electrode on a tissue-contacting portion of at least one of the first jaw 200 and the second jaw 202. Active and return electrodes can be on the same jaw or on opposite jaws. The end effector 124 is thus configured to apply energy to tissue grasped between the first and second jaws 200, 202. Further, because a single jaw can have both an active and a return electrode therein, energy can be delivered to tissue even with the jaws 200, 202 open. The end effector 124 can thus perform a variety of operations, such as spot coagulation, enhanced dissection, and otomy creation, because of the arrangement of the electrodes. Other embodiments of the end effector can have other electrode configurations, such as one or more active electrodes in either or both jaws, one or more return electrodes in either or both jaws, and/or no electrodes on one of the jaws.

The end effector 124 displays at least one location of one or more paths of the electrical energy through the end effector 124. As shown in FIG. 2, the end effector 124 has a plurality of visual indicators 300 on external surfaces of the end effector 124 in the form of minus signs ("−") that indicate electrical return paths through the first and second jaws 200, 202. The end effector 124 also has a plurality of visual indicators 302 on the tissue-contacting surface 220 of the end effector 124 in the form of plus signs ("+") that indicate active electrical paths through the second jaw 202. While plus and minus signs are illustrated in FIG. 2, the visual indicators 300, 302 can take numerous forms, for example pad printed symbols, chemical etchings, dip painting, screen printing, laser engraving, indenting, injection molding, mechanical engraving, abrasive blasting, embossing, coining, solid lines, broken lines, and/or a grid work. The visual indicators are configured to assist users in identifying locations of the electrical paths to help in a variety of operations, such as spot coagulation, enhanced dissection, and otomy creation. The visual indicators can indicate one or more active energy paths and corresponding return paths.

Figure 3:
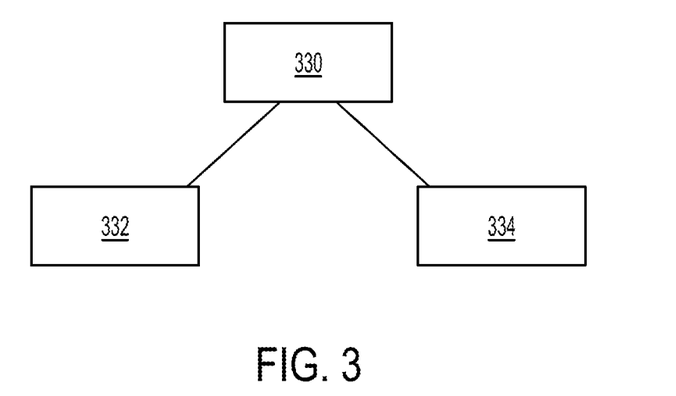
FIG. 3 is a diagram representative of a processor configured to work with the end effector of FIG. 2.

The visual indicators 300, 302 illustrated in FIG. 2 are physically printed on the end effector 124, but the surgical tool 110 can be configured to engage a surgical system, such as the surgical robotic system 100, that is configured to display the at least one location of one or more paths of the electrical energy on a display screen so that the visual indicators are displayed virtually. In such an embodiment, as shown in FIG. 3, the system can use a processor 330, sensor(s) and/or imaging device(s) 332 capable of determining a location and orientation of the end effector (e.g., a camera), and a display 334 for displaying the resulting virtual locations. A combination of real and virtual visual indicators can also be used. The visual indicators can also include one or more lighting sources that illuminate at least one pathway of the electrical energy in one or both of the jaws. The surgical robotic system 100 can be configured to automatically detect location(s) of the visual indicator(s). The end effector can also incorporate a cutting element therein that is configured to cut tissue grasped between the jaws.

Figure 4:
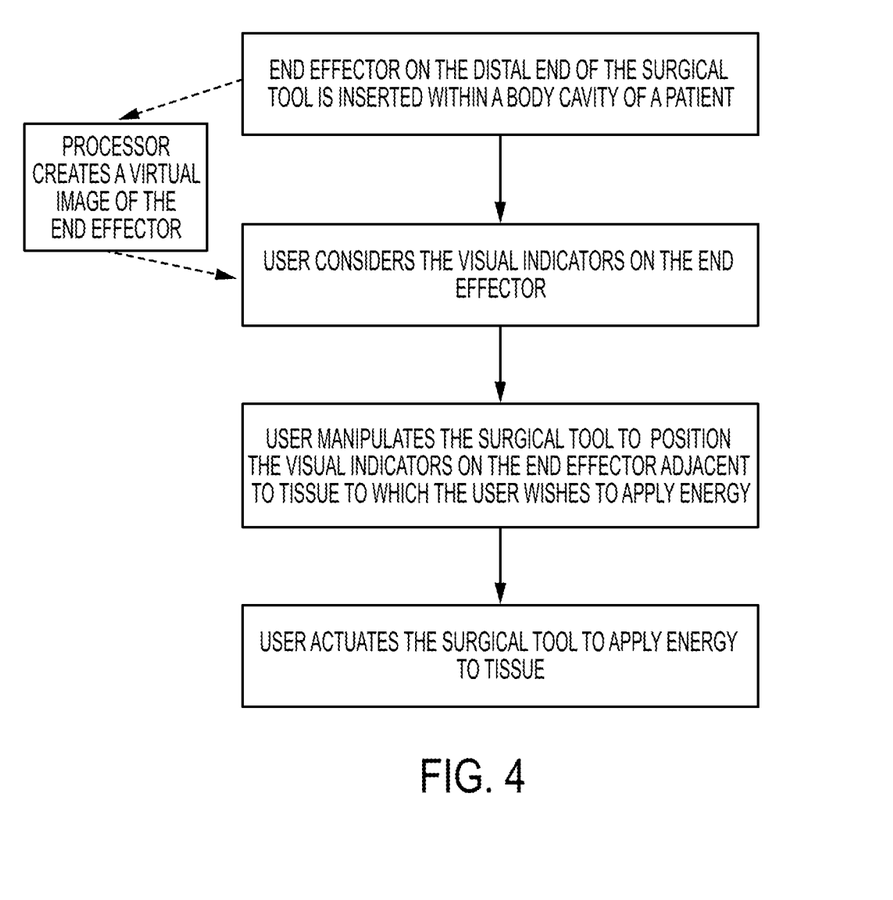
FIG. 4 is a flowchart representative of use of a surgical system that includes the end effector of FIG. 2 in use.

FIG. 4 illustrates a method of using the end effector 124. As shown, the end effector 124 is inserted into a body cavity, aligning the visual indicators 300, 302 with tissue to which a user wishes to apply energy, and actuating the end effector to apply energy to the desired tissue. Optionally, the processor 330 can create a virtual image of the end effector 124 so that virtual electrical energy paths can be displayed and viewed by a user.

End effectors in other embodiments can have other configurations, e.g., scissors, a babcock, a retractor, etc. As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

The systems, devices, and methods disclosed herein can be implemented using one or more computer systems, which may also be referred to herein as digital data processing systems and programmable systems.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical tool, comprising:
an elongate shaft having an end effector at a distal end thereof, the end effector having a first jaw with a first tissue-facing surface and a second jaw with a second tissue-facing surface configured to grasp tissue between the first and second tissue-facing surfaces, the first jaw having an active electrode with a plurality of first indicators on the first tissue-contacting surface, the plurality of first indicators being configured to display at least one location of an active electrical path of the electrical energy through the end effector, the first jaw having a return electrode electrically isolated from the active electrode with a plurality of second indicators on a return surface of the first jaw being configured to display at least one location of a return electrical path of the electrical energy through the end effector, the plurality of second indicators being different than the plurality of first indicators, and the return surface facing away from the second tissue-facing surface;
wherein the first jaw has first and second jaw sides opposite one another and a distal jaw end, the active electrode extends along first and second exterior edges of the first and second jaw sides such that at least one of the plurality of first indicators is visible when the first and second jaws are closed, and the return electrode covers a majority of the first and second jaw sides and the distal jaw end such that at least one of the plurality of second indicators is visible when the first and second jaws are closed.

2. The tool of claim 1, wherein the plurality of first and second indicators being passive indicators comprising at least one of pad printed symbols, chemical etchings, dip painting, screen printing, laser engraving, indenting, injection molding, mechanical engraving, abrasive blasting, embossing, coining, broken lines, solid lines, and a grid work.

3. The tool of claim 1, further comprising a system having a processor, a display, and at least one camera, wherein the system is configured to virtually display the active path and the return path of the electrical energy on the display.

4. The tool of claim 1, wherein the end effector comprises a plurality of teeth on one of the first and the second jaw, and a corresponding groove configured to receive the teeth on the other of the first and the second jaw.

5. The tool of claim 1, wherein the end effector comprises one or more lighting sources configured to illuminate at least one of the active and return electrical paths therethrough.

6. The tool of claim 1, further comprising:
a plurality of teeth protruding along the second tissue-facing surface of the second jaw and extending toward the first jaw;
a corresponding groove formed through the first tissue-facing surface of the first jaw and configured to receive the teeth of the second jaw, the groove having first and second side surfaces extending along the first jaw and a bottom surface facing the second tissue-facing surface of the second jaw; and a plurality of protrusions extending perpendicularly from the bottom surface of the groove and toward the second tissue-facing surface of the second jaw, the plurality of protrusions formed within the groove along the first and second side surfaces of the groove;

wherein the first and second jaws are configured to open and close, the plurality of protrusions are distinct from the first and second side surfaces of the groove such that the plurality of protrusions directly contact only the bottom surface of the groove when the first and second jaws are open, and the plurality of teeth and the plurality of protrusions are configured to directly contact one another along corresponding side surfaces when the first and second jaws are closed.

7. The tool of claim 1, wherein the end effector comprises one or more lighting sources configured to continuously illuminate the active and return electrical paths therethrough both when the electrical energy is active and inactive.

8. A surgical tool, comprising:
a housing;
an elongate shaft extending distally from the housing and having an end effector coupled to a distal end thereof, the end effector having first and second jaws being configured to open and close to grasp tissue and apply energy thereto the first jaw has first and second jaw sides opposite one another and a distal jaw end; and
a plurality of first indicators on a tissue contacting surface of the first jaw configured to indicate an active electrode on the tissue contacting surface from which energy is configured to be applied to tissue, and a plurality of second indicators on a second surface of the first jaw configured to indicate a return electrode on the second surface into which energy is configured to be received from the tissue, the plurality of second indicators being different than the plurality of first indicators, the second surface being positioned on a portion of the first jaw such that the second surface is not between the first and second jaws when the first and second jaws are closed;
wherein the active electrode extends along first and second exterior edges of the first and second jaw sides such that at least one of the plurality of first indicators is visible when the first and second jaws are closed, and the return electrode covers a majority of the first and second jaw sides and the distal jaw end such that at least one of the plurality of second indicators is visible when the first and second jaws are closed.

9. The surgical tool of claim 8, wherein the at least one of the plurality of first and second indicators comprises at least a plurality of passive visual markings.

10. The surgical tool of claim 8, wherein at least one of the plurality of first indicators and the plurality of second indicators comprises at least one of pad printed symbols, chemical etchings, dip painting, screen printing, laser engraving, indenting, injection molding, mechanical engraving, abrasive blasting, embossing, coining, broken lines, solid lines, and a grid work.

11. The surgical tool of claim 8, wherein the end effector includes a cutting element configured to translate therethrough to cut tissue grasped by the end effector.

12. A surgical method, comprising:
applying energy to tissue from an active electrode on a first surface of a first jaw on an end effector of a surgical tool, the active electrode corresponding to a plurality of active electrical energy pathways through the first jaw, the first surface having a plurality of first indicators thereon to visually identify the active electrode, and subsequently receiving at least some of the energy applied to the tissue at a return electrode on at least a second surface of the first jaw, the return electrode corresponding to a plurality of return electrical energy pathways through the end effector, the second surface having a plurality of second indicators thereon to visually identify the plurality of second locations, and the second surface facing away from a contact surface on a second jaw of the end effector;
wherein the first jaw has first and second jaw sides opposite one another and a distal jaw end, the active electrode extends along first and second exterior edges of the first and second jaw sides such that at least one of the plurality of first indicators is visible when the first and second jaws are closed, and the return electrode covers a majority of the first and second jaw sides and the distal jaw end such that at least one of the plurality of second indicators is visible when the first and second jaws are closed.

13. The method of claim 12, wherein at least one of the plurality of first indicators and the plurality of second indicators comprises at least one of pad printed symbols, chemical etchings, dip painting, screen printing, laser engraving, indenting, injection molding, mechanical engraving, abrasive blasting, embossing, coining, broken lines, solid lines, and a grid work.

14. The method of claim 12, further comprising releasably and replaceably coupling the surgical tool to a robotic surgical system.

15. The tool of claim 1, wherein the return surface comprises a plurality of planar surfaces, the first tissue-contacting surface is a planar surface, and the plurality of planar surfaces of the return surface are not parallel to the planar surface of the first tissue-contacting surface.

16. The tool of claim 1, wherein the return surface comprises a plurality of planar surfaces, the first tissue-contacting surface is a planar surface, and the plurality of planar surfaces of the return surface are approximately perpendicular to the planar surface of the first tissue-contacting surface.

17. The surgical tool of claim 8, wherein the tissue contacting surface of the first jaw is configured to apply energy to tissue when the first and second jaws are open.

18. The method of claim 12, further comprising, after applying energy to tissue from the plurality of first locations, closing the first and second jaws to grasp tissue between the first surface of the first jaw and the contact surface on the second jaw of the end effector.

* * * * *